United States Patent [19]

Saruta et al.

[11] Patent Number: 5,171,963
[45] Date of Patent: Dec. 15, 1992

[54] LASER PROCESSING DEVICE AND LASER PROCESSING METHOD

[75] Inventors: Masahiro Saruta; Tetsuji Sagisaka; Kazunari Maeda; Takumi Yashiki, all of Shizuoka, Japan

[73] Assignee: NTN Corporation, Osaka, Japan

[21] Appl. No.: 700,819

[22] Filed: May 16, 1991

[30] Foreign Application Priority Data

May 21, 1990 [JP] Japan .................................. 2-132204
May 21, 1990 [JP] Japan .................................. 2-132205
Jun. 29, 1990 [JP] Japan .................................. 2-173361

[51] Int. Cl.⁵ .............................................. B23K 26/00
[52] U.S. Cl. ........................... 219/121.69; 219/121.82; 219/121.83
[58] Field of Search ................ 219/121.68, 121.69, 219/121.78, 121.82, 121.83

[56] References Cited

U.S. PATENT DOCUMENTS

| | | | |
|---|---|---|---|
| 4,825,034 | 4/1989 | Auvert et al. | 219/121.83 X |
| 4,918,284 | 4/1990 | Weisz | 219/121.78 |
| 4,964,940 | 10/1990 | Auvert et al. | 219/121.68 X |
| 4,998,005 | 3/1991 | Rathi et al. | 219/121.83 |
| 5,017,755 | 5/1991 | Yahagi et al. | 219/121.68 |
| 5,059,764 | 10/1991 | Baer | 219/121.69 |

Primary Examiner—C. L. Albritton
Attorney, Agent, or Firm—Lowe, Price, LeBlanc & Becker

[57] ABSTRACT

A laser processing device includes a Z stage movable in the up and down directions with respect to a XY stage movable in the X, Y directions on which an object to be processed is provided. The surface of the object to be processed is image-sensed by a CCD camera through a lens of an electrically-driven revolver attached to the Z stage, which is projected in a monitor. When a defect of the object is displayed in the monitor, a laser beam is radiated to a defective portion of the object from a laser head provided in the Z stage and the defective portion is removed.

9 Claims, 6 Drawing Sheets

LASER PROCESSING DEVICE AND LASER PROCESSING METHOD

BACKGROUND OF THE INVENTION

1. Field of the Invention

The present invention relates to a laser processing device and a laser processing method. More particularly, the present invention relates to a laser processing device for and a laser processing method of inspecting a liquid crystal display panel for a defect, for example, and removing the defect by radiating a laser beam to the defective portion.

2. Description of the Background Art

The liquid crystal display panels are coming in frequent use for various kinds of electronic equipments in these days. Also, the quantity of information displayed in a liquid crystal display panel has been increasing, so that liquid crystal display panels with high display density are in demand. In order to increase the display density, it is required to thin wiring patterns between liquid crystal indicators and terminals and also to narrow intervals between adjacent patterns.

When the density of the pattern is increased, however, patterns adjacent to each other may be electrically connected because of insufficient etching in the etching process of the patterns. A liquid crystal repair device is used for detecting such defects and producing good products. In a conventional liquid crystal repair device, a liquid crystal display panel to be inspected is provided on a stage, and a head movable in the directions of X, Y, and Z is provided thereabove, to which a CCD camera and a laser beam source are attached. The wiring patterns are image-sensed by the CCD camera. An operator, while observing it in a monitoring television, finds out a portion in which adjacent patterns are connected with each other, to which portion a laser beam emitted from the laser beam source is radiated to burn off the defective portion between patterns.

In order to find out a defective portion of a liquid crystal panel with such a liquid crystal repair device, the XY stage must be moved so that the portion objective to the inspection is brought in a center portion of a visual field. To move the XY stage, instructions are made by manually operating a transport handle or by electrically operating switches. There has been a problem, however, that it is troublesome for an inspector in a conventional manual transport handle method, and that the operation efficiency is not good. Handle operation causes a problem of vibration, especially when observing at a high magnification. In the electrical method, if a stage travel speed is relatively high, the XY stage cannot be stopped at a specified position due to over running in many cases. The tendency is especially strong when observing it at a high magnification. Furthermore, in a conventional liquid crystal repair device, there has been a disadvantage that the holding stiffness is low because the head in which the CCD camera and the laser beam source are provided is made movable in the X, Y directions.

SUMMARY OF THE INVENTION

Accordingly, it is an object of the present invention to provide a laser processing device and a laser processing method with increased holding stiffness of a head, which is capable of inspecting an object to be processed such as a liquid crystal display panel for defects.

Another object of the present invention is to provide a laser processing device and a laser processing method which are stable with the holding stiffness increased by fixing an optical axis of a laser beam source.

Still another object of the present invention is to provide a laser processing device having a control circuit of an XY stage capable of moving a specific portion of an object to be inspected into a central portion of a visual field quickly with a simple operation.

Briefly stated, the present invention includes a laser processing device for inspecting an object to be processed for a defect and removing the defect by radiating a laser beam thereto, in which a laser beam is radiated from a laser beam source with its optical axis fixed with respect to a plane direction to an object to be processed supported on a table movable in a plane direction, and the condition of processing the object to be processed is observed with an optical system.

Accordingly, in accordance with the present invention, the table is movable in a plane direction and the laser beam source is provided at a portion fixed with respect to the plane direction, so that the holding stiffness can be increased.

In accordance with another aspect of the present invention, a defect detecting circuit is provided for inspecting an object to be processed on a table for a defect, and a defective position on the object to be processed is determined in accordance with a detection output thereof and the present position on the plane of the table.

In accordance with still another aspect of the present invention, a defective position on the object to be processed can be found out easily.

In accordance with a further aspect of the present invention, when an arbitrary position of the object to be processed and enlargement magnification are specified in a screen of a monitor, a table moves so that the specified position is located in the center of the monitor and also the magnification of a lens is switched to the specified enlargement magnification.

In accordance with yet another aspect of the present invention, a specified position of the object to be processed can be observed in a center portion of a monitor while being enlarged, which further facilitates observation of a defective portion.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
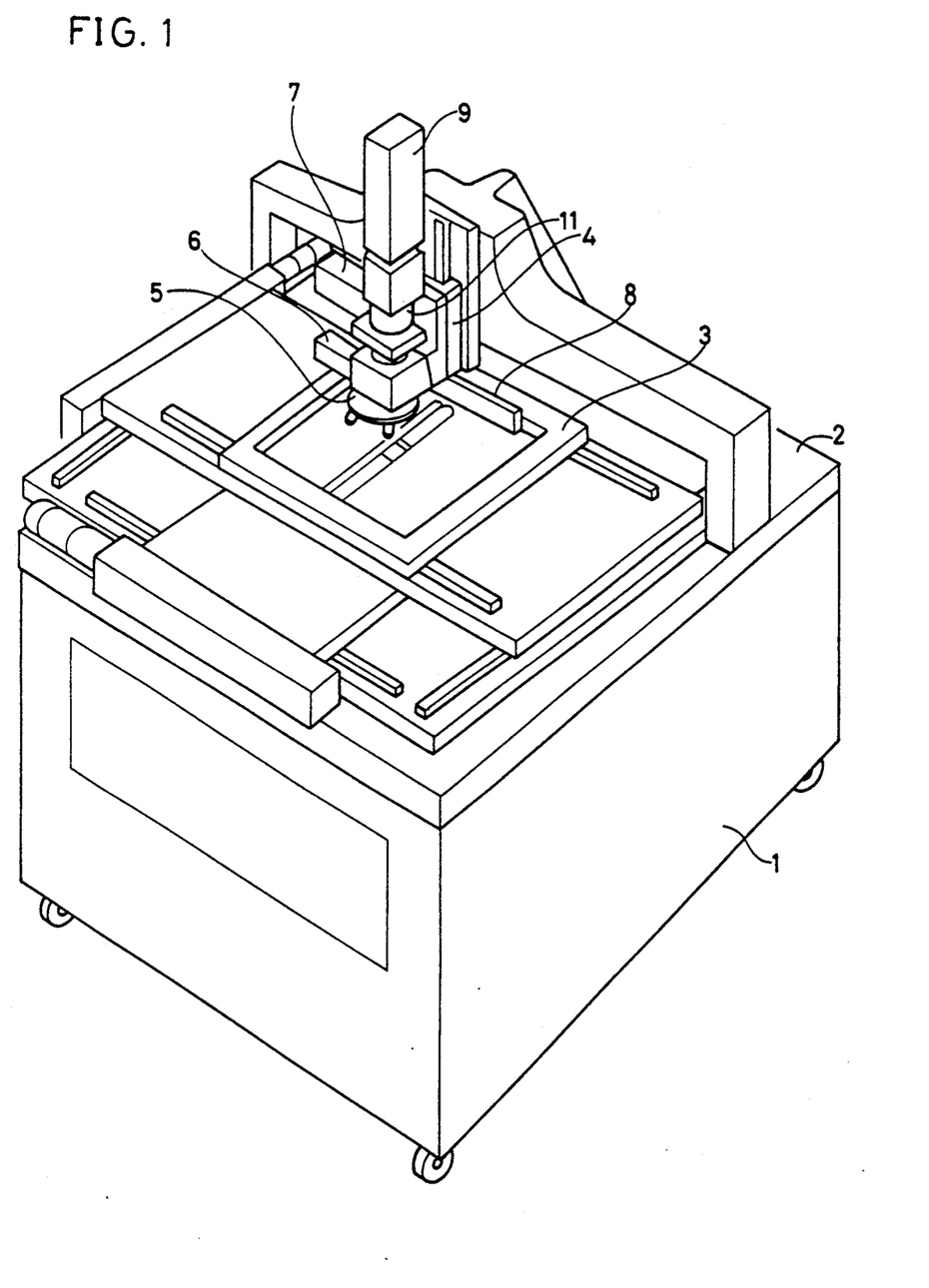
FIG. 1 is a perspective view of an appearance of one embodiment of the present invention.
Figure 2:
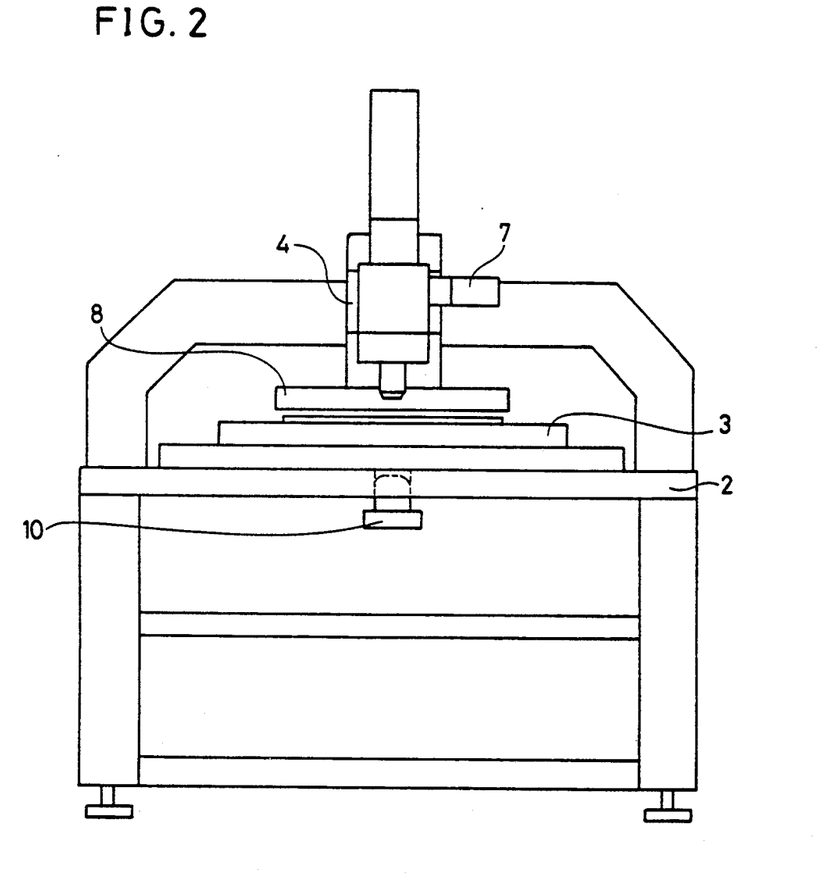
FIG. 2 is a front view of one embodiment of the present invention.

FIG. 1 is a perspective view of the appearance of one embodiment of the present invention, and FIG. 2 is the front view.

Referring to FIGS. 1 and 2, an XY stage 3 movable in a plane, in the X, Y directions, is provided above a base 2 of a casing 1. On the XY stage 3, a liquid crystal panel as an object to be processed is provided. A Z axis table 4, movable only in the Z direction (up and down directions) while movement in the XY directions is forbidden, is provided for inspecting an object to be processed provided on XY stage 3. In the Z axis table 4, an electrically-driven revolver 5, a microscope 11, a light source 6 for microscope lightening, a CCD camera 7, a defect inspection device 8 and a laser head 9 are provided. The electrically-driven revolver 5 includes lenses with different magnifications, one of which is selected by with the driving force of a built-in motor, microscope 11 is used for observing an object to be processed and focusing a laser beam, and the light source 6 for microscope lightening illuminates an object to be processed.

CCD camera 7 image-senses the surface of the object to be processed through a lens of electrically-driven revolver 5. Defect inspection device 8 is for inspecting the object to be processed for defects, which includes a linear image sensor. Laser head 9 radiates an infrared laser beam onto the surface of the object to be processed and applies processing thereto. A light source 10 for irradiating the object to be processed in a transmissive manner is provided below XY stage 3 as shown in FIG. 2.

Figure 3:
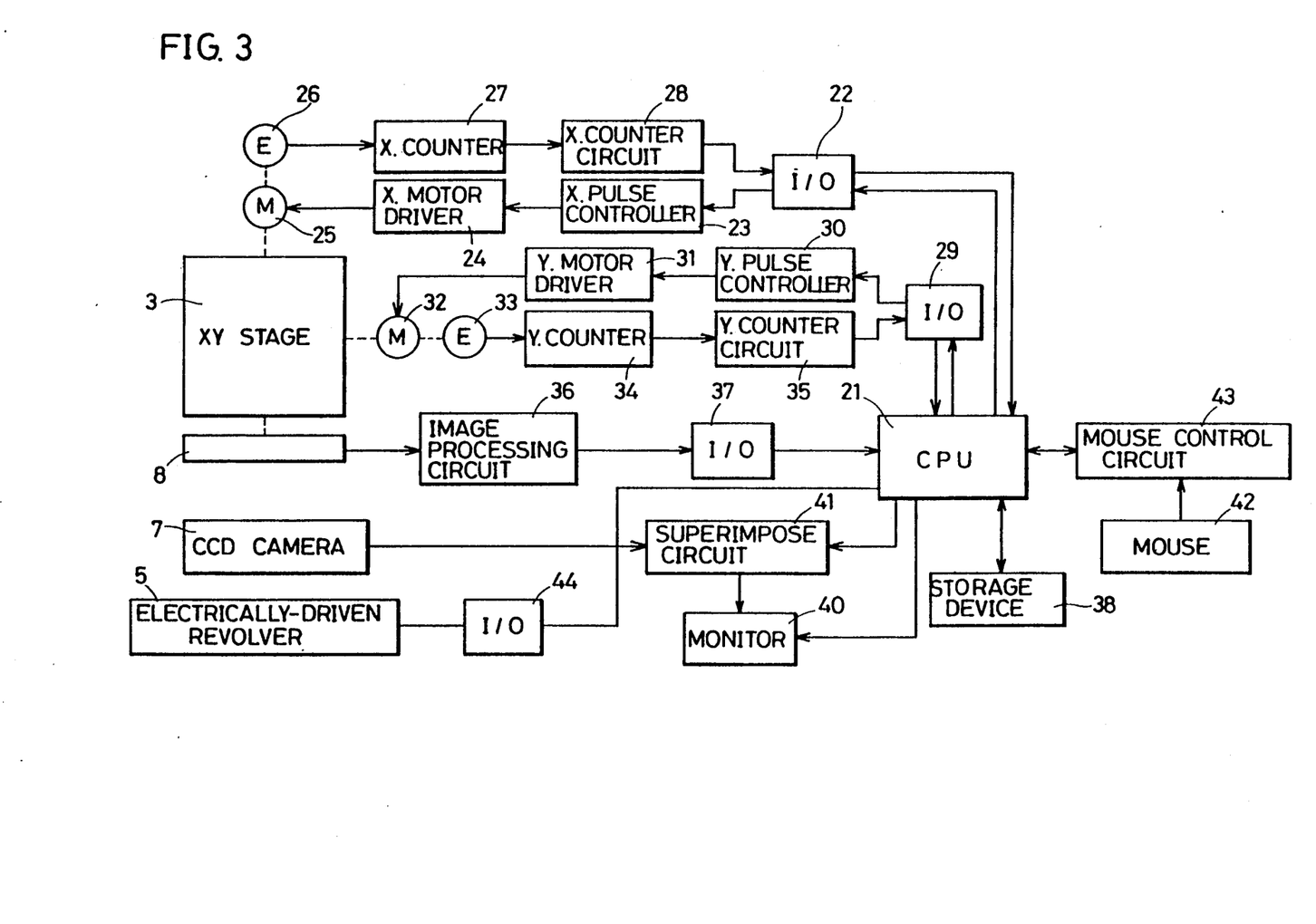
FIG. 3 is a schematic block diagram of one embodiment of the present invention.

FIG. 3 is a schematic block diagram of one embodiment of the present invention. Next, referring to FIG. 3, the electric structure of one embodiment of the present invention will be described. CPU 21 controls the entirety according to a program stored in a built-in memory. That is, CPU 21 gives a command signal for moving XY stage 3 in the X direction to an X pulse controller 23 through an I/O 22. X pulse controller 23 produces an X pulse in response to the command signal. The X pulse is given to an X motor driver 24. X motor driver 24 rotates an X motor 25 corresponding to the number of given pulses. X motor 25 moves XY stage 3 in the X direction. The number of rotations of X motor 25 is detected by an X encoder 26. X encoder 26 produces pulse signals corresponding to the rotation of X motor 25 and provides the same to X counter 27. X counter 27 counts the pulse signals, of which counted output is given to CPU 21 through an X counter circuit 28 and I/O 22.

In the same way, CPU 21 gives a command signal for moving XY stage 3 in the Y direction to a Y pulse controller 30 through an I/O 29. Y pulse controller 30 produces Y pulses corresponding to the command signal and gives the same to a Y motor driver 31. Y motor driver 31 rotates a Y motor 32 corresponding to the number of Y pulses. Y motor 32 is provided for moving XY stage 3 in the Y direction. The number of times of rotation of Y motor 32 is detected by a Y encoder 33, and pulse signals corresponding to the number of times of rotation are given to a Y counter 34. Y counter 34 counts the pulse signals and gives the counted output to CPU 21 through a Y counter circuit 35 and I/O 29.

CPU 21 determines a position of XY stage 3 in the X direction and the Y direction with the counted outputs of X counter circuit 28 and Y counter circuit 35.

Linear image sensor 8 as a defect inspection device 8 outputs defects of the object to be processed as picture element information and gives it to an image processing circuit 36. Image processing circuit 36 image-processes outputs of defect inspection device 8 and gives the defect picture element information to CPU 21 through I/O 37. CPU 21 operates on the defect picture element information and counted output of Y counter circuit 35 to calculate defect position information, which is stored in a storage device 38. The defect position information is displayed in a monitor 40.

CCD camera 7 image-senses an object to be processed located on XY stage 3, and gives the output to a superimpose circuit 41. Superimpose circuit 41 superimposes a video signal which is an output of CCD camera 7 on an image signal of a computer given from CPU 21 to display the composite image on monitor television 40. A control signal is supplied to electrically-driven revolver 5 from CPU 21 through an I/O 44. In electrically-driven revolver 5, a motor provided inside is driven according to the control signal to switch lenses. A command signal is provided to CPU 21 from a mouse 42 through a mouse control circuit 43.

Figure 4:
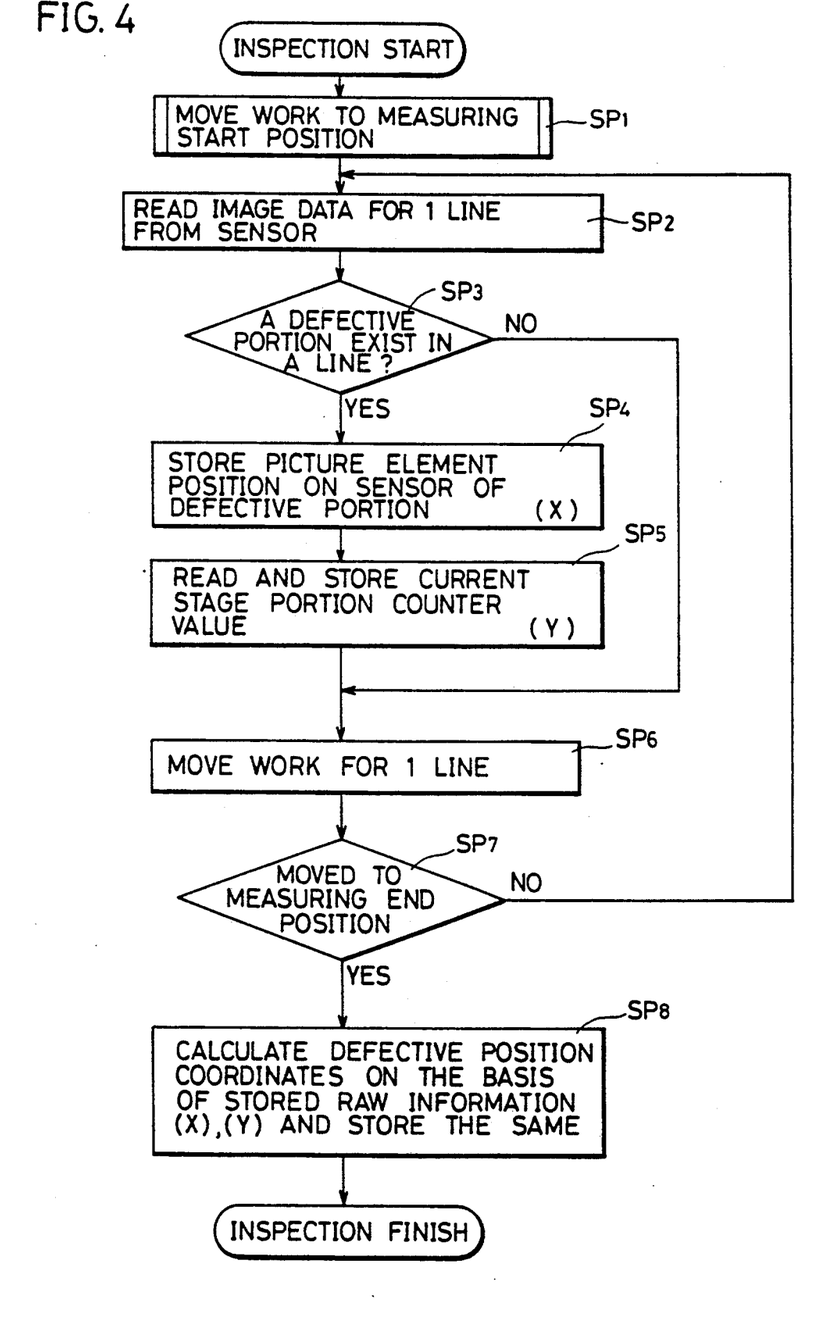
FIG. 4 is a flow diagram for describing operation of one embodiment of the present invention.
Figure 5:
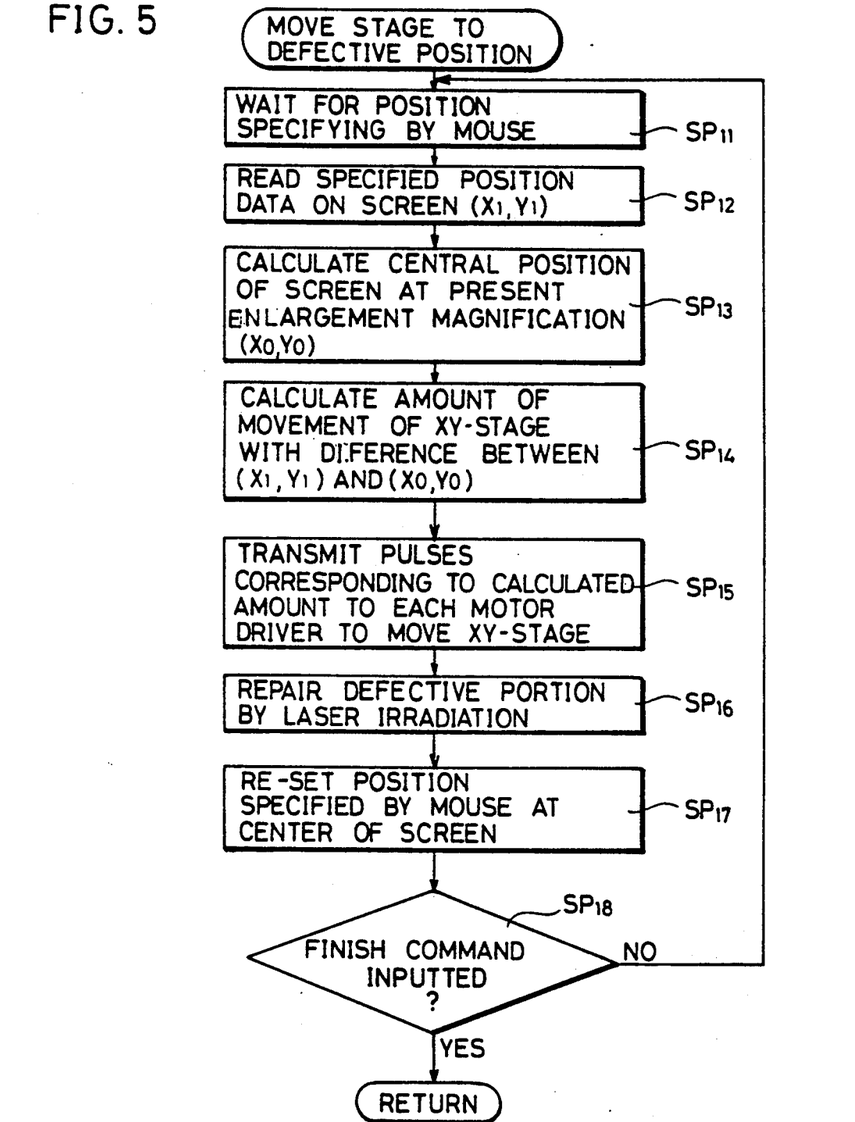
FIG. 5 is a flow diagram for describing operation in FIG. 4 of detecting a defective picture element position and then moving a portion to be repaired in the defective picture element to a laser irradiation position.
Figure 6:
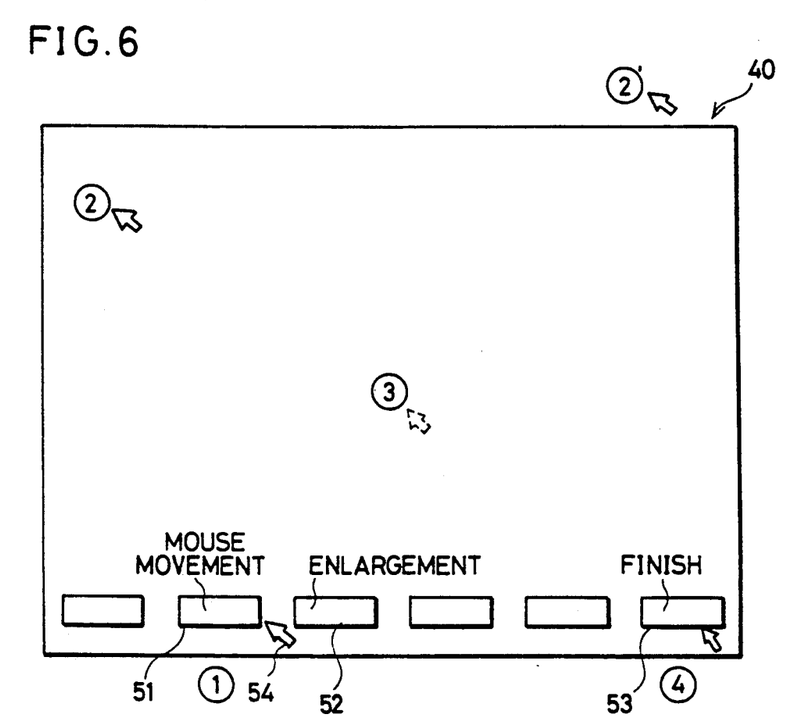
FIG. 6 is a diagram showing one example of an image displayed in a monitor screen in accordance with one embodiment of the present invention.
Figure 7A:
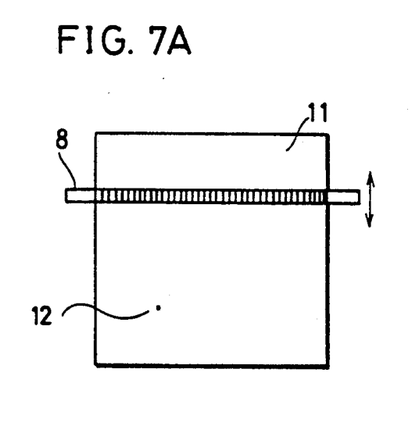
FIGS. 7A and 7B are diagrams for describing the defect inspection in accordance with one embodiment of the present invention.
Figure 7B:
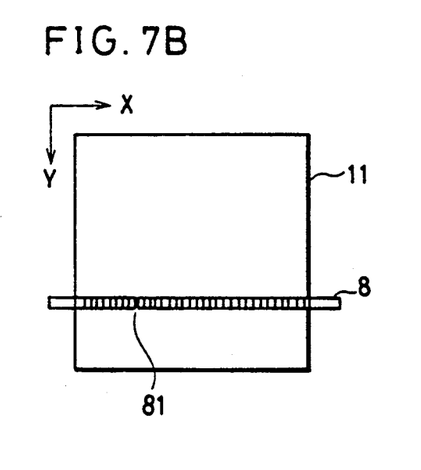

FIG. 4 is a flow chart for describing operations of an inspection process in one embodiment of the present invention, FIG. 5 is a flow diagram for describing operations for detecting a defective picture element position and then moving a portion to be repaired in the defective picture element to a laser irradiation position, FIG. 6 is a diagram showing one example of an image displayed in a monitor screen in accordance with one embodiment of the present invention, and FIGS. 7A and 7B are diagrams for describing a defect inspection in accordance with one embodiment of the present invention.

Next, referring to FIGS. 1-7B, specific operations of one embodiment of the present invention will be described.

After moving an object to be inspected to a measuring start position in step (simply referred to as SP in the figure) SP1 of the main routine shown in FIG. 4, in step SP2, defect inspect device 8 reads an image on the surface of the object to be processed. The image signal is image-processed by image processing circuit 36, which is given to CPU 21 through I/O 37. CPU 21, as shown in FIG. 7A, reads image data for 1 line in the X direction on the object 11. CPU 21, in step SP3, makes a determination as to whether there is a defect portion in the 1 line or not according to the read image data. If there is no defect, CPU 21 outputs a command signal for moving the object for 1 line in step SP6.

If a determination is made that there is a defect in the 1 line, CPU 21 stores a picture element position of the defect portion on the sensor in the linear image sensor in step SP4. That is, as shown in FIG. 7B, when defect inspect device 8 detects a defect 12 on the object to be processed, an output, of the liner image sensor of a portion corresponding to the position, changes. CPU 21 recognizes the X coordinate of the defect position from the position of picture element 81.

CPU 21, in step SP5, determines the present position of XY stage 3 according to the counted output of Y counter circuit 35 and stores the same. CPU 21 then outputs a command signal in order to move the object for 1 line in the Y direction in step SP6. In step SP7, CPU 21 makes a determination as to whether XY stage 3 is moved to a measurement end position or not, and if it has not moved to the end position, it returns to step SP2 again to repeat operations of steps SP2-SP7. Repeating the operations, when a determination is made that it has moved to the measuring end position, in step SP8, on the basis of the stored picture element position of the defect portion on the sensor in the X direction and the position of XY stage 3 in the Y direction, defect position coordinates are calculated, which is stored in storage device 38 and also displayed in monitor 40.

Next, on the basis of the defective position information (which picture element is defective), the stage is moved to the defective picture element to be repaired. Subsequently, the method for moving the stage to locate the defective portion in the picture element (a portion to be repaired in a picture element) at the laser irradiation center will be described referring to FIG. 5.

First, in step SP11, it is stood by until a position specifying signal is inputted from mouse 42 through mouse control circuit 43. On the screen of television monitor 40, the object of inspection image-sensed by CCD camera 7 is displayed, and furthermore, as shown in FIG. 6, a mouse movement command 51, an enlargement command 52 and a finish command 53 are displayed, and an image of an arrow 54 indicating a specify point of mouse 42 is also displayed.

Moving an arrow of mouse 42 to the position of mouse movement command 51, and depressing a key provided in mouse 42, a mouse movement command 51 is specified. Then, in the object of inspection, a portion to be displayed in a central portion of the screen of monitor television 40 is specified by the arrow 54 of the mouse. If, as shown by the arrow ②', the arrow 54 of the mouse is drawn in the direction out of the screen, XY stage 3 moves to follow it in that direction.

Subsequently, CPU 21, in step SP12, when a position specify signal is inputted from mouse 42 through mouse control circuit 43, reads the coordinates (X, Y) specified by the arrow 54 of the mouse (i.e., the position of the defective portion to be subjected to repair) on the screen of monitor television 40. CPU 21 determines the present position of XY stage 3 with counted values of X counter 27 and Y counter 34 and calculates a central position coordinates $(X_0, Y_0)$ of the screen according to the current enlargement magnification of electrically-driven revolver 5 in step SP13. By specifying enlargement command 52 with mouse 42, an arbitrary enlargement magnification can be specified. That is, when enlargement command 52 is specified by mouse 42, CPU 21 gives a control signal to electrically-driven revolver 5 through I/O 44, drives a motor provided inside and switches lenses to the one of specified magnification.

CPU 21 calculates the travelled amounts in the X direction and the Y direction of XY stage 3 from the difference between coordinates $(X_1, Y_1)$ and $(X_0, Y_0)$ in step SP14. CPU 21 supplies as outputs pulse signals, the number of signals corresponding to the calculated quantities of travel in the X direction and the Y direction, to Y pulse controller 30 and X pulse controller 23 through I/O 22 and 29 in step SP15. Y motor driver 31 drives Y motor 32 corresponding to the number of pulses given from Y pulse controller 30, and X motor driver 24 drives X motor 25 corresponding to the number of pulses given from X pulse controller 23. In this condition, a laser is irradiated to repair the defective portion in step SP16.

Subsequently CPU 21 makes a specified position of mouse 42 located in the center of monitor television 40 in step SP17. In step SP18, CPU 21 determines as to whether finish command 53 shown in FIG. 6 is indicated by mouse 42 or not, and if finish command 53 is not indicated, it returns to step SP11, and if finish command 53 is indicated, it returns to the main flow.

As described above, by specifying an arbitrary position (a defective portion) of the object of inspection displayed in the display screen of monitor television 40 by mouse 42, that position is displayed in the center of the display screen of monitor television 40, which facilitates repair of defects of the object to be inspected.

As described above, Z axis table 4 in which CCD camera 7, laser head 9 and so forth are provided is moved only in the Z direction and XY stage 3 on which an object to be processed is moved in the X direction and the Y direction to inspect for defects of the object to be processed, so that the holding stiffness of Z axis table 4 can be increased. Furthermore, by detecting picture elements of a defective position by scanning the object to be processed with defect inspection device 8 including a linear image sensor, a defect position on the object to be processed can be detected in a digital manner by CPU 21 and can be stored.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A laser processing device for inspecting an object to be processed for a defect by radiating a laser light to remove the defect, comprising;
    a laser beam source having its optical axis fixed with respect to a plane direction for emitting said laser beam;
    a table movable in a plane direction with respect to said laser beam for supporting said object to be processed;
    an optical system for observing a condition of processing of the object to be processed on said table;
    defect detecting means for inspecting the object to be processed for a defect on said table; and
    determining means for determining a defect position on said object to be processed according to a detection output of said defect detecting means and the present position in a plane on said table.

2. The laser processing device according to claim 1, wherein said laser beam source comprises means for emitting an infrared laser beam for removing a defect of the object to be processed on said table.

3. The laser processing device according to claim 1, wherein said optical system comprises;
    a lens changeable in magnification for taking in an image of said object to be processed, and
    image-sensing means for image-sensing the image taken in by said lens.

4. The laser processing device according to claim 3, further comprising display means for displaying the image image-sensed by said image-sensing means.

5. The laser processing device according to claim 4, further comprising:
    specifying means for specifying an arbitrary position of said object to be processed on a display surface of said display means, and control means for moving said table in response to specifying said arbitrary position of said object to be processed by said specifying means so that said arbitrary position of said table is located in the center of said display means.

6. The laser processing device according to claim 1, wherein said specifying means comprises means for specifying an enlargement magnification, and said control means comprises means for switching the magnification of said lens to said specified enlargement magnification in response to specifying said enlargement magnification by said specifying means.

7. A laser processing device for inspecting an object for a defect and radiating a laser beam to remove a detected defect, comprising:

a laser beam source having its axis fixed with respect to a plane direction for emitting said laser beam;

a table movable in a plane direction with respect to said laser beam for supporting said object;

an optical system including means for controlling (i) optically scanning said object on said table and providing a first output signal, (ii) determining defects in said object in response to said first output signal, (iii) calculating defect position coordinates for the determined defects, (iv) storing said defect position coordinates, and (v) outputting an image signal corresponding to said defect position coordinates; and display means for displaying said image signal corresponding to said defect position coordinates.

8. The laser processing device according to claim 7, further comprising:

a lens changeable in magnification for taking in an image of said object on said table; and image-sensing means for image-sensing the image taken in by said lens and providing a second output signal to said display means, said display means displaying a composite image of said second output signal and said image signal corresponding to said defect position coordinates.

9. The laser processing device according to claim 8, further comprising:

means for specifying an arbitrary position of a display surface of said display means while displaying said composite image; and control means for moving said table in response to the specified arbitrary position of said display surface to position the specified arbitrary position in the center of said display means.

* * * * *